US006994983B2

(12) United States Patent
Ens (10) Patent No.: US 6,994,983 B2
(45) Date of Patent: Feb. 7, 2006

(54) KITS FOR DETERMINATION OF THROMBOXANE B₂ METABOLITE AND OPTIMIZING ASPIRIN DOSAGE

(75) Inventor: Gordon E. Ens, Denver, CO (US)

(73) Assignee: Esoterix, Inc. Coagulation, Aurora, CO (US)

( * ) Notice: Subject to any disclaimer, the term of this patent is extended or adjusted under 35 U.S.C. 154(b) by 197 days.

(21) Appl. No.: 10/157,431

(22) Filed: May 28, 2002

(65) Prior Publication Data

US 2003/0124615 A1 Jul. 3, 2003

Related U.S. Application Data

(63) Continuation-in-part of application No. 09/619,211, filed on Jul. 19, 2000, now abandoned.

(60) Provisional application No. 60/161,462, filed on Oct. 25, 1999.

(51) Int. Cl.
*C12Q 1/56* (2006.01)
(52) U.S. Cl. .......................... 435/13; 435/7.1; 435/975
(58) Field of Classification Search ................. 435/13, 435/7.1, 7.72, 967, 975; 424/9.2
See application file for complete search history.

(56) References Cited

U.S. PATENT DOCUMENTS 5,538,901 A * 7/1996 Law et al. ................. 436/501

FOREIGN PATENT DOCUMENTS

JP 64-13459 * 1/1989

OTHER PUBLICATIONS

Takasaki, W. Enzyme Immunoassay of Human Plasma 11-Dehydrothromboxane B2. Thrombosis Research vol. 63, 331-341, 1991.*
Pemeby C. Optimization of an Enzyme Immunoassay for 11-Dehydrothromboxane B2 in Urine: Comparison with GC-MS. Thrombosis Research vol. 96, 427-436, Jun. 15, 1999.*
Williams S. Better increase in Fibrin Gel Porosity by Low Dose Than Intermediate Dose Actylsalicyic Acid. European Heart J 19(11)1666-1672, 1998.*
Juul-Moler S., Edvardsson N., Jahnmatz B., et al., Lancet 1992; 340:1421.
ISIS-2 Collaborative Group; ISIS-2, Lancet 1988; 2: 349.
The Dutch TIA Study Group, N. Engl. J. Med. 1991; 325:1261.
Hirsh J., Dalen J.E., Fuster V., Harker L.B., Patrono C., Roth G., Chest 1995; 108 Suppl.: 247s.
International Stroke Trial Collaborative Group, Lancet 1997; 349: 1569.
CAST (Chinese Acute Stroke Trial) Collaborative Group, Lancet 1997; 349: 1641.
The Medical Research Council's General Practice Research Framework, Lancet 1998;351:233.
Hansson L., Zanchatti A., Carruthers S.G., et al., Lancet 1998; 351:1755.
Fitch L.L., Buchwald H., Matts J.P., Am. Heart J. 1995; 129: 656.
Antiplatelet Trialists' Collaboration, BMJ 1994; 308: 81.
Hennekens C.H., Peto R., Hutchinson G.B., et al., N. Engl. J. Med. 1988; 318:923.
Manson J.E., Stampfer MI, Colditz G.A., et al., JAMA 1991; 266: 521.
Ridker P.M., Manson J.E., Buring J.E., Muller J.E., Hennekens C.H., Circulation 1990;82:897.
Buring J.E., Hennekens C.H., J. Myocardial Ischemia 1992; 4: 27.
Roderick P.J., Wilkes H.C., Meade T. W., Br. J. Clin. Pharmacol 1993; 35: 219.
Petroski D., Lancet 1997; 349: 430.
Peto R., Gray R., Collins R., et al., BMJ 1988; 296: 313.
Kronmal RA., Hart RG., Manolio T.A., Stroke 1998; 29: 887.
He J., Whelton P.K., Vu B., Klag MI, JAMA 1998; 280: 1930.
Patrona C., Coller B., Dalen J., et al., Chest 1998; 114 Suppl:470s.
Helgason C.M., Hoff J.A, Kindos G.T., Barce L.D., Stroke 1993; 24:1458.
Ridker P.M., Cushman M., Stampfer M.J., Tracy R.P., Hennekens C.H. Circulation 82(3) 1990 p 897-899.
Wu K.K., Hoak J.C., Lancet 11;1974:924.
Trip M.D., Cats V.M., Van Capelle F.J.L., Vreeken J., New Engl. J. Med. 1990, 322:1549.
Helgason C.M., Bolin K.M., Hoff J.A., et al., Stroke 1994; 25: 2331.
Pappas J.M., Westengard J.C., Bull B.S., Arch. Path. Lab. Med. 1994; 118: 801.
Mueller M.R., Salat A., Stangl P., Thromb. Haemost 1997; 78: 1003.

(Continued)

*Primary Examiner*—Ralph Gitomer
(74) *Attorney, Agent, or Firm*—Baker & McKenzie LLP (57) ABSTRACT

Kits are provided that can be used to determine a thromboxane B₂ metabolite level and a creatinine level in a biological sample, particularly a human urine sample. This information can be used to optimize aspirin dosage in a patient. The present invention further includes calibrant preparations. In some embodiments, these calibrants comprise urine, particularly human urine that is identified in repeated trials to provide a consistent and reproduceable level of thromboxane B₂ metabolite. As such, they function as control preparations that reduce error from intra-assay sampling measurements.

12 Claims, 8 Drawing Sheets

OTHER PUBLICATIONS

Grotemeyer KH., Scharafinski H.W., Husstedt I.W., Thrombos. Res. 1993; 71:397.

Komiya T., Kudo M., Urabe T., Mizuno Y., Stroke 1994; 25: 2337.

Israels L.G., Activation of Permeabilized Platelets by Inositol-1, 4,5-Triphosphate, Thrombus Res 40 499-509 1985.

Rifkin R.M., Effect of Dipyridamole and RA 233 on Human Platelet Function in Vitro Thrombus D. H 1978 vol. 29 694-700.

Vane J.R., Botting RM., Semin. Arthr. Rheum. 1997; 25 Suppl. 1: 2.

Lawson JA., Patrono C., Ciabattone G., et al., Anal. Biocem. 1986, 155: 198.

Schror K., Semin. Thrombos. Hemostas. 1997; 23: 349.

Weber A.A., Zimmennann K.C., Meyer-Kirchrath J., Schror K., Lancet 1999;353: 900.

Pedersen A.K, Fitzgerald G.A., New Engl. J Med. 1984; 311: 1206.

Schmidt E.B., Dyerberg J., Drugs 1994; 47: 405.

Weber P., Dendich A., Machlin L.J., Nutr. 1997; 13: 450.

O'neil C.K., Avila J.R., Fetrow C.W., Nursing 1999; 58.

Jannsen P.L.T.M.K., Akkeman J.-W.N., Hoilman P.C.H., Van Staveren W.A., Zwaginga J-J, Katan M.B., Eur. J. Clin. Nutr. 1995; 49:365.

Beving H., Eksborg S., Malmgren R.S., et al., Thrombos. Res. 1994; 74:39.

Buerke M., Pittroff W., Meyer J., Darius H., Am. Heart J. 1995; 130:465.

May J.A., Heptinstall S., Cole A.T., Hawkey C.J., Thrombos. Res. 1997; 88: 183.

Samuelsson B., Granstrom E., Green K., et al., Ann. Rev. Biochem. 1975;44:669.

Catella F., Fitzgerald G.A., Thrombos. Res. 1987; 47:647.

Catella F., Healy D., Lawson J.A., et al., Proc. Natl. Acad. Sci. USA 1986; 83: 5861.

Van Kooten F., Ciabattoni G., Koudstaal P.J., Dippel W.J., Patrono C., Stroke 1999;30:546.

Lellouche F., Fradin A., Fitzgerald G., et al., Prostaglandins 1990; 40: 297.

* cited by examiner

Figure 7  PURR for baseline and post-81 mg aspirin

| Baseline mean : 1669 | Post-81 mg aspirin mean: 537 | Percent inhibition: 68% | p = 0.00000419 |

Figure 8 : PURR for baseline and post-325 mg aspirin

| Baseline mean : 1669 | Post-325 mg aspirin mean: 440 | Percent inhibition: 74% | p = 0.0000000192 |

KITS FOR DETERMINATION OF THROMBOXANE B₂ METABOLITE AND OPTIMIZING ASPIRIN DOSAGE

RELATED APPLICATION

This application is a continuation-in-part of U.S. application Ser. No. 09/619,211, filed Jul. 19, 2000, now abandoned, which claims the benefit of U.S. Provisional patent application 60/161,462, filed Oct. 25, 1999.

BACKGROUND OF THE INVENTION

Aspirin (acetyl salicylic acid) effectively reduces the risk of secondary thrombotic events in individuals who have experienced angina, myocardial infarction, peripheral artery disease, or cerebrovascular ischemia. Aspirin also may reduce the risk of initial thrombotic events in healthy individuals. For this reason, many individuals, through physician prescriptions or self-medication, take aspirin on a regular basis for the primary or secondary prevention of thrombotic disease.

Some important questions remain unanswered. What long-term dosage of aspirin is likely to confer protection from thrombosis while avoiding gastric discomfort or hemorrhagic conditions? What individuals are "resistant" to aspirin, how may aspirin resistance be identified, and what effect does aspirin resistance have on the interpretation of clinical trials?

Several studies suggest that aspirin, at doses between 30 and 325 mg/day, is effective in reducing the incidence of arterial thrombotic events. Physicians customarily prescribe aspirin to prevent myocardial infarction, cerebrovascular thrombotic disease, and vascular death in individuals with stable angina (1), unstable angina (2), myocardial infarction (3), transient cerebral ischemia, peripheral vascular disease, and thrombotic stroke. (4) For patients with prior acute myocardial infarction or stroke, aspirin prevents up to 40 new thrombotic events per thousand treated. (5) Two large randomized trials demonstrate the thrombosis-reducing efficacy of aspirin for patients with acute ischemic stroke, and aspirin is now routinely prescribed in these conditions. (6,7)

Aspirin has been shown to be effective in prevention of heart disease in men with several high risk clinical conditions and both men and women with hypertension. (8,9) The Program on the Surgical Control of the Hyperlipidemias categorized a number of individuals who had a partial ileal bypass surgery as smokers and non-smokers and assigned them to aspirin and non-aspirin arms. Within this population, the overall mortality rate was 45.2% for smokers with no aspirin use and only 10.4% for those who reported even infrequent aspirin use. (10)

Primary Prophylaxis with Aspirin

Aspirin reduces the incidence of thromboembolic arterial disease in healthy individuals over 50 years of age. (11, 12, 13) In healthy men, aspirin appears to prevent an average of four thrombotic events per thousand subjects treated. In the Physicians' Health Study, healthy men who took 325 mg of aspirin every other day experienced a mean reduction in the incidence of first myocardial infarction of 44.8% compared to those taking placebos. (14) There was a particularly marked reduction of 59.3% for the morning peak of infarction, between 4 and 10 a.m. These findings were not confirmed in the British Doctors' study, however, and additional confirmatory studies are in progress, including the current Women's Health Study. (15)

Aspirin Dosage and Complication

Hemorrhage and Gastrointestinal Toxicity

There is a dose-related risk of gastrointestinal bleeding in aspirin therapy, especially in patients who have coagulopathy or who are taking additional anticoagulant therapy such as heparin or warfarin. (16) This is of particular concern in individuals with stomach lesions such as the ulcers associated with Helicobacter pylori infection. To avoid hemorrhage, many physicians recommend enteric-coated aspirin, especially if the recommended dosage exceeds 325 mg/day. (17) In the British Doctors' Study, where the prescribed randomized dose was 500 mg/day, 20% of aspirin arm participants dropped out due to dyspepsia or constipation, 3.6% experienced bleeding or bruising, and 2.2% had gastrointestinal blood loss. (18)

In the Cardiovascular Health Study, Kronmal, et al found a 1.6× relative risk of ischemic stroke and a 4× relative risk for hemorrhagic stroke for healthy women 65 and older who took aspirin. (19) This study presents self-reported, not randomly assigned, aspirin users and illustrates the hemorrhagic risk of high-dose aspirin in particular disease situations.

For patients who have an elevated risk of thrombosis, the absolute benefit of aspirin prophylaxis clearly outweighs the relatively small risk of bleeding. However, in the individuals with no risk factors, aspirin dosages must be carefully monitored to avoid gastric discomfort, gastric hemorrhage, systemic hemorrhage and hemorrhagic stroke.

Recommendations for Therapeutic Aspirin Usage

Because of the preponderance of evidence favoring the protective effects of aspirin's against arterial thrombosis, millions rely on aspirin prophylaxis daily either by physician's prescription or self-medication. In a review of clinical studies undertaken in the 1980s and 1990s, Hirsh, Dalen, Fuster, et al make the following recommendations: (4)

Aspirin is indicated for patients with stable angina, unstable angina, acute myocardial infarction, transient cerebral ischemia, thrombotic stroke, and peripheral arterial disease.

A dose of 75 to 100 mg/day should be used chronically for all indications, although an initial dose of 160 to 325 mg should be used in acute settings.

For patients with cerebrovascular disease, a dose of 75 mg/day is effective.

Aspirin at 100 mg/day is indicated for patients with prosthetic heart valves who develop systemic embolism while on warfarin.

Aspirin is indicated for patients with atrial fibrillation in whom warfarin is contraindicated.

There is no recommendation either for or against aspirin usage in normal, healthy adults, and no standards have been established for laboratory monitoring of aspirin's efficacy, a growing concern as clinicians became aware of aspirin resistance and interindividual pharmacokinetic variations.

Recent clinical investigations indicate that approximately 10% to 15% of patients on aspirin therapy for prevention of thrombosis have a less than adequate platelet suppression response. (20) Additionally, it is reported that some individuals develop an increasing resistance over time. (21) It is uncertain if this observed resistance is the result of poor absorption, changes in pharmacodynamics, non-compliance, or mechanisms not currently identified. Ridker, et al reported that the positive effect of aspirin appears to be altered by underlying inflammation and further suggested that markers of inflammation such as C-reactive protein may delineate those individuals who will respond atypically to aspirin. (22)

Platelet Activity Studies and Variable Aspirin Response

Current laboratory measures of platelet activation include the Mielke template bleeding time, aggregometry, lumiaggregometry, the Date-Behring PFA-100 platelet function analyzer, and the platelet reactivity test. (23) While the platelet-suppressing property of aspirin clearly affects the results of these procedures in general, individuals' laboratory responses to aspirin therapy are idiosyncratic. Trip et al. report 46% of patients with positive spontaneous platelet aggregation results suffered a repeat myocardial infarction. (24) This was the first study that paired clinical outcomes with laboratory results. Helgason, et al demonstrated that seven of 17 patients with atrial fibrillation achieved only partial inhibition of platelet aggregation when taking 325 mg of enteric coated aspirin per day. Non-compliance had no statistical effect on this study's outcome. Helgason's group further demonstrated that 8.2% of patients with previous ischemic stroke exhibited restoration of platelet aggregation (aspirin resistance) despite escalation of aspirin dosage to, ultimately, 1300 mg/day. (25)

Pappas, et al used a specially designed visual platelet aggregate inspection technique to measure the response to the inhibitory effects of aspirin in 31 healthy young adults. (26) They demonstrated a wide inter-individual variation in response to aspirin that was consistent over 28 days of aspirin ingestion. Mueller, et al performed corrected whole blood aggregometry on patients with intermittent claudication who were taking 100 mg aspirin/day after elective peripheral balloon angioplasty. (27) At any given time, only 40% of males showed complete inhibition of aggregation. Significantly, non-responsive aggregometry results in this study predicted increased risk of reocclusion, leading to the conclusion that aspirin may fail to protect partial- and non-responders from occlusive events.

Grotemeyer, et al performed whole platelet reactivity tests on 180 internal carotid artery stroke victims given 500 mg of aspirin three times per day. (28) All began with elevated platelet reactivity immediately following stroke. Upon initial aspirin administration, 90% of the subjects demonstrated an immediate suppression of platelet reactivity. However, 60 patients' platelets resumed enhanced platelet reactivity only twelve hours after the initial aspirin dosage. These were termed secondary aspirin non-responders. Over a 24-month period following discharge, 24 (40%) of the secondary aspirin non-responders experienced myocardial infarct, repeat stroke, or vascular death p<0.0001). Of 114 remaining subjects (six were lost to follow-up), only five (4.4%) suffered these major endpoints. Grotemeyer concluded that early identification of secondary aspirin non-responders is an important step to effective prevention of further thrombotic events in post-stroke patients. In an extensive review of aspirin and platelet laboratory studies, Patrono, et al, comments that 10% to 15% of individuals have a poor initial response or demonstrate progressive resistance to aspirin. No large clinical trials have incorporated laboratory measures of platelet activation, so the effect of aspirin resistance on clinical outcomes is currently unknown.

Komiya, et al used platelet aggregometry to detect cases of aspirin therapy non-compliance and incorrect dosage. They found that 10% of 159 outpatients' results were outside the diagnostic parameters because of non-compliance and that an additional 2% were confirmed compliant but still had normal aggregometry results. (29) Their study illustrates the necessity for monitoring aspirin therapy in patients who may be suspected of non-compliance.

Aspirin Suppresses Platelet Activity

Agonists Trigger Platelet Activation

Figure 1:
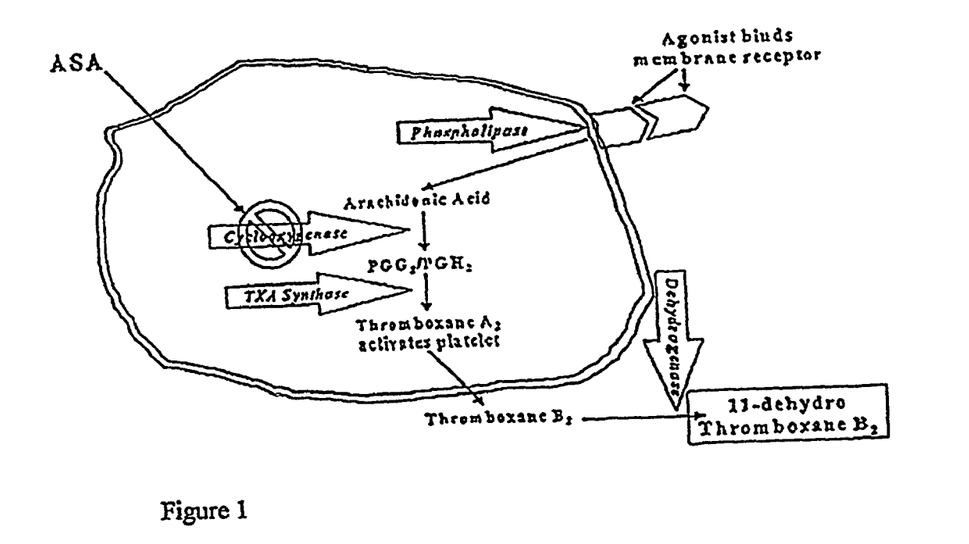
FIG. 1—Biochemical pathway in a cell showing release of 11-dehydro thromboxane B2 from thrombozanes Bs.

The cyclooxygenase (COX) biochemical activation pathway, as diagrammed in FIG. 1, is essential to normal platelet activation and to the prevention of systemic hemorrhage. (30) COX is also an important activation enzyme in other cells.

Activation begins when a platelet agonist such as ADP, epinephrine, collagen, or thrombin binds to its platelet membrane receptor site. This activates phospholipase $A_2$ and frees arachidonic acid, a 20-carbon unsaturated fatty acid, from its supporting membranes phospholipid. Free arachidonic acid is a substrate for the COX pathway. (31)

The Platelet Cyclooxygenase Pathway

COX, a membrane-associated endoperoxide synthase with two catalytic sites, rapidly modifies the free arachidonic acid in a two-step process. (32) The first catalytic site converts it to the endoperoxide $PGG_2$. The second site, a peroxidase-type site, converts the short-lived $PGG_2$ to $PGH_2$. $PGH_2$ is then converted by the isomerase action of thromboxane synthase to thromboxane $A_2$ ($TXA_2$), which activates the platelet.

$TXA_2$ is rapidly hydrolyzed to thromboxane $B_2$($TXB_2$), a stable plasma product of the COX pathway. $TXB_2$, in turn, is converted to a variety of end products, most of which are excreted via the kidney. (33)

Aspirin Irreversibly Acetylates Cyclooxygenase

Platelets (and other cells) are now known to produce two isoforms of COX-1 and COX-2. (34) COX-1 is a constitutive membrane-bound enzyme that functions in all normal platelets, whereas COX-2 is a cytokine-inducible enzyme that appears in newly produced platelets and in other cells during inflammation.

Figure 2:
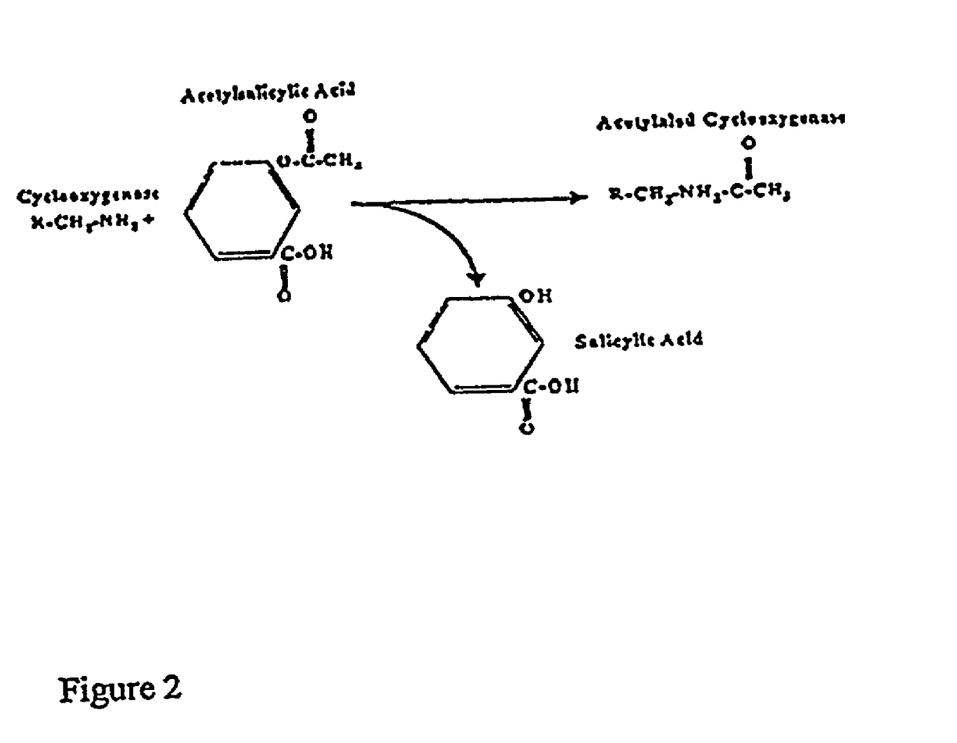
FIG. 2—Biochemical pathway showing the reaction products, salicylicacid and acetylated cycloxiggonance from cyclocygenase and acetylsalicylic acid.

Aspirin irreversibly acetylates both COX-1 and COX-2 at serine 529, see FIG. 2. For the COX-1 enzyme, the attached acetyl group sterically hinders arachidonic acid's access to its reactive site. Acetylation does not appear to hinder the activity of COX-2. The inflammation-induced activity of COX-2 in platelets may account for some cases of aspirin resistance (35), as may pharmacokinetic variations among individuals.

Aspirin Pharmacokinetics

Aspirin is rapidly absorbed from the stomach and duodenum and is rapidly hydrolyzed to salicylic acid by esterases in the gut, liver, and erythrocytes. Because only aspirin, not salicylic acid, acetylates COX-1 (or COX-2), a significant proportion of acetylation occurs in the presystemic circulation of the gut and liver. (36). Salicylic acid circulates bound to plasma proteins for up to six hours and is cleared by the kidney.

Platelets acetylated during the time of peak aspirin levels lose most of their ability to be activated; as reflected in prolonged bleeding times, reduced aggregometry responses, and diminished $TXB_2$ production. A single dose of 325 mg aspirin is detectable within minutes using these laboratory assays and the effects remain for six to ten days. Platelets with acetylated COX-1 survive normally and continue to participate in the adhesion reaction. Normal platelet function test results are restored only when a predominant population of new platelets has been released from the bone marrow.

Additional Platelet Activity-Suppressing Substances

Other non-steroidal anti-inflammatory drugs (NSAIDs) such as dipyridamole, sulphinpyrazone, and ibuprofen act upon COX-1 or other platelet enzymes, but no clinical trials have established antithrombotic properties for these drugs. Ticlopidine, clopidegril, and abiximab exert their antiplatelet activity on membrane receptors. The effects of all these therapeutics may be measured using aggregometry, lumiaggregometry, and plasma, serum, or urine $TXB_2$ assays.

In addition, many dietary components and supplements have been shown to modify platelet function by unknown mechanisms. These include fish oil (37), vitamin E (38), garlic (39), red wine, and purple grape juice (40). Herbal and dietary supplements may both interfere with or enhance the effect of aspirin on platelets.

Janssen, et al provided healthy volunteers with 3 mg of aspirin per day, a study designed to mimic acetylsalicylic acid levels in certain plants. (41). They showed that serum $TXB_2$ levels were reduced by 39% compared to placebo.

A number of prospective randomized clinical trials have demonstrated that 50 to 500 milligrams of aspirin per day effectively reduces the risk of primary or secondary arterial thrombotic events in many individuals. Recognition of aspirin's antithrombotic properties has promoted clinical researchers to focus substantial efforts towards modifying platelet function with not only aspirin but a variety of newly developed platelet-suppressive drugs.

Despite the availability of these new drugs, the use of aspirin for arterial thrombosis prevention continues to increase as public awareness grows. More than 80 billion aspirin tablets are consumed annually in the USA, and more than 37% of the individuals taking aspirin do so to "prevent blood clots". Additionally, individuals who employ alternative medicine practices may consume significant quantities of red wine, purple grape juice, fish oil, vitamin E, garlic, ginkgo biloba, and other substances known to interfere with platelet function.

Numerous reports in the scientific literature detail varied individual responses to aspirin dosages. However, little is reported regarding the potential need to adjust aspirin dosage according to individual biologic response or to a changing response over time. Limited studies correlate the occurrence of thrombotic events with individuals who become "resistant" to aspirin.

| Subject | 3 | 8 | 12 | 14 | 17 | 18 | 24 |
|---|---|---|---|---|---|---|---|
| % Inhibition (81) | 60 | 78 | 46 | 48 | 70 | 17 | 10 |
| % Inhibition (325) | 44 | 40 | 82 | 83 | 46 | 83 | 38 |

Why hasn't aspirin, the drug most widely consumed to modify platelet function, been dosed according to biologic response, in a manner similar to anticoagulants? Because most laboratory tests used to monitor platelet function are time consuming, require expensive equipment (platelet aggregometer), or are traumatic to the patient (bleeding time). In addition, all current assay methods are subject to wide variation in results due to preanalytical and analytical variables, inherent in all ex vivo tests that require the patient's platelets.

SUMMARY OF THE INVENTION

The present invention, in a general and overall sense, provides a method for identifying an optimal minimal aspirin dose for a patient that is specifically tailored to the patient's specific platelet response levels (i.e., to monitor platelet inactivation).

The method includes measurement of thromboxane $B_2$ metabolite levels in the patient to determine the optimum dose for platelet inhibition, with minimum aspirin related side-effects. It is envisioned that the invention, in one aspect, may also be provided in a test kit form. In some embodiments, the kit will be provided together with a solid substrate that is at least partially coated with a material such as an antibody, that is capable of reacting with a thromboxane $B_2$ metabolite, such as 11-dehydro $TXB_2$. Also included would be a reactor fluid, such as one that would change in color upon exposure to the thromboxane $B_2$ metabolite.

BRIEF DESCRIPTION OF THE DRAWINGS

FIG. 9 is a histogram that illustrates the separation between the non-aspirin and aspirin population.

FIG. 10 illustrates results form seven subjects whose response to 81 or 325 mg aspirin was "weak" (less than 50%). Note that subjects 12, 14, 18, and 24 responded better to 325 mg, while subjects 3, 8, and 17 responded better to 81 mg, illustrating the idiosyncratic nature of aspirin response and possible resistance.

DETAILED DESCRIPTION OF THE PREFERRED EMBODIMENTS

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Measuring Platelet Activation

Platelet Aggregometry and In Vitro Activation

One may detect and measure in vitro platelet activation using aggregometry, which detects platelet aggregation; lumiaggregometry, which detects both aggregation and platelet-specific secretions; or platelet-activation instrumentation such as the Date-Behring PFA-100 platelet function analyzer.

Platelet Activation Metabolites and In Vitro Activation

Plasma, serum, or urine assays of platelet secretions and arachidonic acid pathway metabolites may be employed in the detection of in vitro platelet activation. Assays of plasma or serum $TXB_2$ are used extensively in platelet function research laboratories where specimen management is carefully controlled, but routine clinical measurement is hampered by the in vitro instability of platelets.

Aspirin Dosage and Measures of Platelet Activity

Measurement of aspirin-induced platelet suppression has led to some unexpected findings. Using the arachidonic acid metabolite 12-L-5, 8, 10 - heptadecatrienoic acid (12-HHT) as marker, Beving et al measured aspirin's suppression of platelet activity at three dosages, 30, 75 and 150 mg/day. (42) His group demonstrated that, after seven days' treatment, discontinuing the higher dosages triggered a rebound phenomenon. This was reflected in significantly elevated 12-HHT levels persisting for up to six weeks after stopping aspirin therapy. Further, they demonstrated the rebound to be greater in patients whose baseline levels of 12-HHT were elevated. They concluded that the degree of platelet suppression and ultimate rebound effect could be controlled by determining the pre-aspirin platelet activity via 12-HHT level analysis and by adjusting aspirin dosage accordingly. The rebound effect did not occur in the 30 mg/day dosage arm.

Buerke et al used bleeding times, platelet aggregometry, and serum $TXB_2$ assays to demonstrate effective aspirin dosages in healthy males. (43). Comparing various dosage combinations, they recommended a loading dose of 300 mg aspirin in combination with 40 mg/day as a maintenance dose to achieve optimum suppression of platelets. Loading dosages of 40 or 100 mg failed to elicit significant changes within two hours of administration.

The Urinary Activation Marker 11-dehydro thromboxane $B_2$

Whole blood or plasma specimens for platelet metabolite assays require special management because the platelets tend to become activated by changes in temperature, exposure to non-biological surfaces, and mild mechanical agitation. Aggregometry assays are qualitative and technology-intensive, and bleeding time tests have poor predictive values. Thus, it is necessary to locate a metabolite formed in vivo from the products of platelet activation (45).

Hepatocyte 11-hydroxy thromboxane dehydrogenase acts upon plasma $TXB_2$. (46) The plasma half-life of 11-dehydro $TXB_2$ is 45 minutes, and plasma levels remain in the nanogram range, as it is rapidly cleared by the kidney. (47) The urine concentration of 11-dehydro $TXB_2$, however, is plentiful and, as platelets appear to be its only source, proportionally reflects platelet activity within the previous twelve hours. (46) Urine levels of 11-dehydro $TXB_2$ are frequently elevated in atherosclerosis, the chronic phase following stroke, transient ischemic attack, intracerebral hemorrhage, and atrial fibrillation. (48) Further, 11-dehydro $TXB_2$ levels are typically decreased in aspirin therapy, even in cases of atherosclerosis, myocardial infarction, and atrial fibrillation.

Assays for 11-dehydro $TXB_2$ have intra- and interassay CVs of $\leq 10\%$ and do not cross-react with $TXB_2$, 2, 3-dimer $TXB_2$, nor other cyclooxygenase metabolites (49).

EXAMPLE 2

11-dehydro $TXB_2$ in Randomly Collected Urine From Aspirin and Non-Aspirin Donors Urine 11-dehydro $TXB_2$ was assayed in random urine specimens to:
- Establish a reference range in non-aspirin users.
- Determine whether aspirin therapy is related to levels below the reference range.
- Detect aspirin resistance in individuals taking aspirin therapy.

11-dehydro $TXB_2$ Reference Range and results in Aspirin Treatment

Random urine specimens were collected from 65 individuals who had avoided aspirin for at least two weeks and from 45 individuals who were taking 81 or 325 mg/day by prescription. Each specimen was assayed for 11-dehydro-$TXB_2$. Specimens were assayed at two dilutions using acetylcholinesterase-linked immunoassay. The results were tested for parallelism and averaged. Urine creatinine was assayed using the Jaffe picrate reaction. To normalize for urinary output, results were expressed in pg 11-dehydro $TXB_2$/mg creatinine. Results of all populations were compared using the student t-test. Within-day variation is 30% and day-to-day variation 20%.

Figure 3:
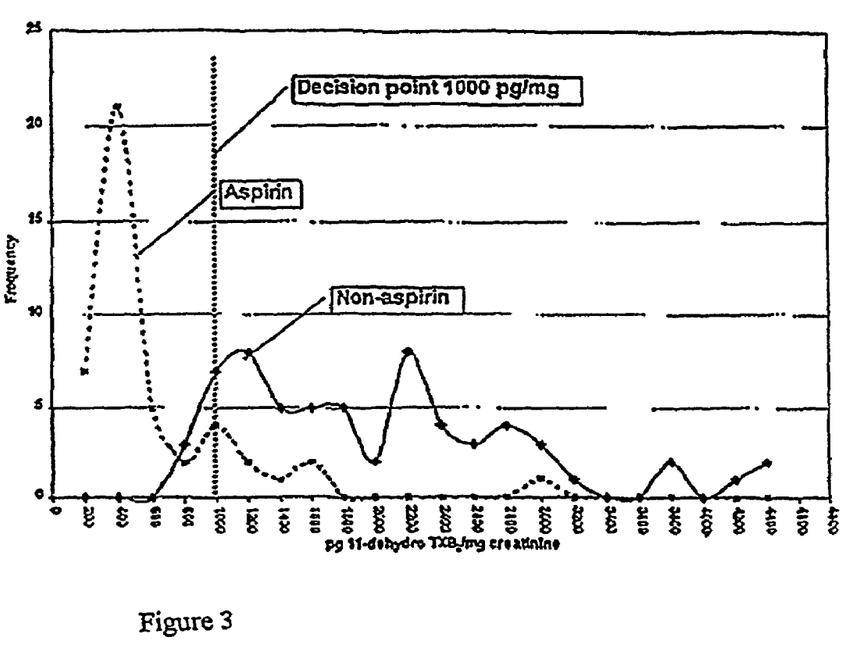
FIG. 3—dehydro $TXB_2$/mg creatinine (x axis) vs. frequency (y axis).

A decision point of 100 pg 11-dehydro-$TXB_2$/mg creatine yields both false negative and false positive rates of 10%, the best achievable combination, as shown in Table 1. Aspirin effect is ruled in at a decision point of 800 pg/mg or less and ruled out of 1000 pg/mg. FIG. 3 is a histogram that illustrates the clear separation between the non-aspirin and aspirin A decision point of 1000 pg 11-dehydro-$TXB_2$/mg creatinine yields both false negative and false positive rates of 10%, the best achievable combination, as shown in Table 1. Aspirin effect is ruled in at a decision point of 800 pg/mg or less and ruled out of 1000 pg/mg. FIG. 3 is a histogram that illustrates the clear separation between the non-aspirin and aspirin

TABLE 1

| | Decision level in pg/mg | False Positive rate for aspirin effect | True Positive Rate for Aspirin effect | True Positive Rate for aspirin effect | False Negative rate for aspirin effect |
|---|---|---|---|---|---|
| Aspirin rule-in | 600 | 0.0% | 75.6% | 100.0% | 24.4% |
| | 700 | 0.0% | 80.5% | 100.0% | 19.5% |
| ≦800 pg/mg | 800 | 0.0% | 80.5% | 100.0% | 19.5% |
| | 900 | 1.8% | 85.4% | 98.2% | 14.6% |
| Recommended Decision point | 1000 | 10.5% | 90.2% | 89.5% | 9.8% |
| | 1100 | 17.5% | 90.2% | 82.5% | 9/8% |
| | 1200 | 24.6% | 95.1% | 75.4% | 4.9% |
| | 1300 | 29.8% | 97.6% | 70.2% | 4.9% |
| | 1400 | 33.3% | 97.6% | 66.7% | 2.4% |
| Aspirin rule-out | 1500 | 35.1% | 100.0% | 64.9% | 0.0% |
| | 1600 | 42.1% | 100.0% | 57.9% | 0.0% |

TABLE 1-continued

| Decision level in pg/mg | False Positive rate for aspirin effect | True Positive Rate for Aspirin effect | True Positive Rate for aspirin effect | False Negative rate for aspirin effect |
|---|---|---|---|---|
| ≤1500 pg/mg | | | | |

EXAMPLE 3

Figure 4:
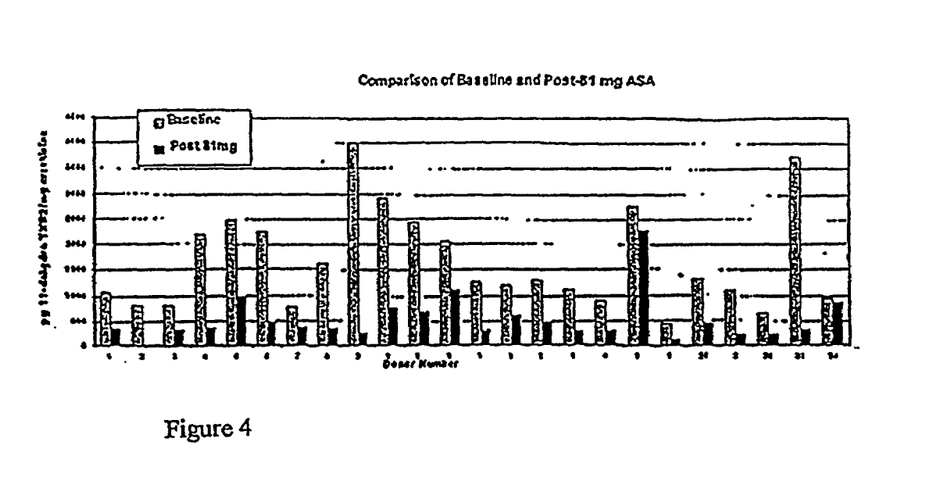
FIG. 4—Comparison of baseline and post-81 mg aspirin and for baseline and post-81 mg ASA. pg. 11-dehydro $TXB_2$/mg creatinine (x axis) vs. donor numbers (y axis).
□=Baseline
■=Post 81 mg FIG. 5—Comparison of baseline and post-81 mg aspirin and for baseline and post-325 mg ASA-pg. 11-dehydro $TXB_2$/mg creatinine (x axis) vs. donor numbers (y axis).
□=Baseline
■=Post 325 mg FIG. 6—pg $TXB_2$/mg creatine (x axis) vs. Subjects (y axis)
□=Baseline
■=Post 81 mg
(Shaded Box) □=Post 325 mg FIG. 7—Comparison of baseline and post-81 mg aspirin and for baseline and post-81 mg ASA FIG. 8—Comparison of baseline and post-325 mg aspirin and for baseline and post-325 mg ASA FIG. 9—Frequency distribution of non-aspirin and aspirin subjects demonstrating the decision point of 400 PURR units—Histogram Comparison of Aspirin and Non-Aspirin Donors.
Figure 5:
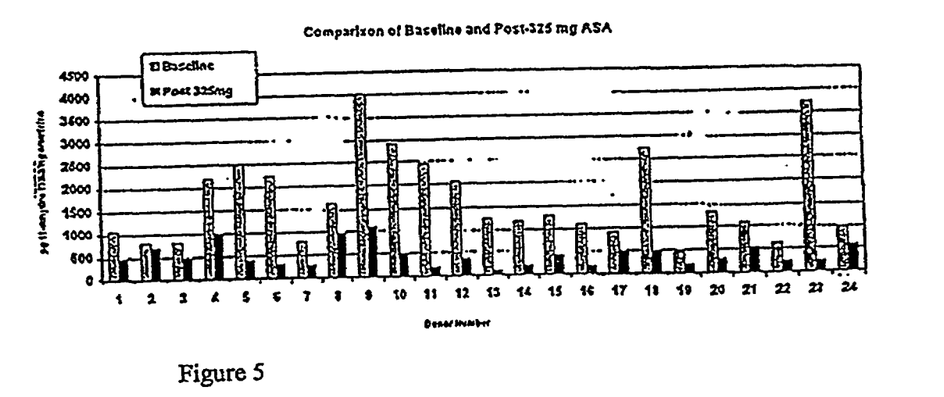
Figure 6:
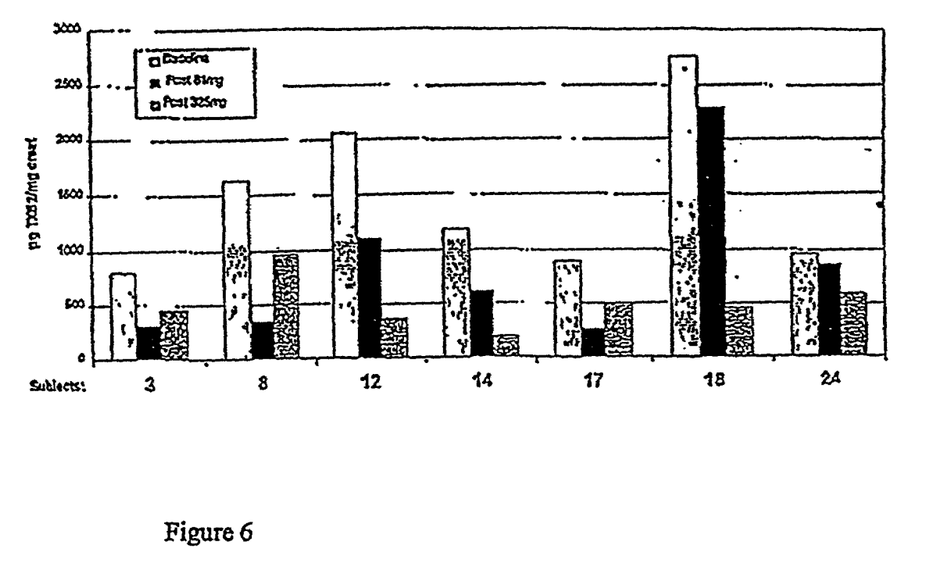

Effect of Aspirin on the 11 Dehydro $TXB_2$ Level of Healthy Non-Aspirin Users Initiation of aspirin therapy causes mean reduction of 68% for 81 mg/day and 76% for 325 mg/day as illustrated in FIGS. 4 and 5. There was no significant difference between the 81 mg/day and 325 mg/day suppression levels.

An immunoassay is provided here that measures the effect of aspirin on platelet function. A stable metabolite of the platelet activation process, 11-dehydro-$TXB_2$, can be measured in random urine, bypassing the need for ex vivo platelet function. Utilizing this assay, a significant difference individuals taking 81 or 325 mg of aspirin and individuals not taking aspirin was demonstrated. Values equal to or less than 400 pg 11-dehydro-$TXB_2$/mg creatinine indicates that aspirin in usage is sufficiently inhibiting COX-1 activity. Aspirin users with levels over 500 pg/mg appear to be resistant and not achieving optimal platelet inhibition, as demonstrated in FIG. 3. Utilizing these decision point criteria, 13% of individuals were identified as potential non-responders.

The present findings demonstrate that the range of non-aspirin results is broad and appears bimodally distributed. The higher peak represents increased platelet activation.

From the crossover study, seven individuals (30%) had a less than 50% response to either 81 mg or 325 mg of aspirin. Of these, three demonstrated less 11-dehydro $TXB_2$ excretion at 81 mg than at 325 mg. However, one individual (subject 24) did not demonstrate 50% reduction to 81 mg or 325 mg of aspirin suggesting aspirin resistance. The inhibitory contribution of dietary and lifestyle habits should always be taken into consideration when interpreting data and may have contributed to these results. Further, urine metabolite interference, exercise, and hormonal variation may be responsible for a 20–30% within-day and day-to-day variation.

Aspirin antithrombotic therapy is long-term therapy. The urine 11-dehydro $TXB_2$ assay is a readily available means for evaluating individual response to aspirin. It is useful for detecting aspirin resistance and for prescribing and monitoring alternative therapies. The assay is also useful in monitoring patient compliance and determining the lowest aspirin dose that produces effective COX-1 inhibition while avoiding aspirin's unpleasant, sometimes dangerous side effects.

Using the 11-dehydro $TXB_2$ assay as the measure of platelet activity, clinical trials will be conducted that 1) further compare biologic response to aspirin's affect on clinical outcomes, 2) evaluate whether dosage adjustment according to COX-1 inhibition will reduce thrombotic events while limiting untoward side effects, and 3) determine whether the influence of inflammatory process, reflected by abnormal C-reactive protein levels, are associated with aspirin resistance.

Aspirin has been proven to prevent secondary arterial thrombosis in a variety of conditions, and may be used as defined here to prevent primary heart attacks and strokes to those who are at risk. Proper monitoring of aspirin therapy will lead to more accurate dosing, prevention of side effects, and the management of aspirin resistance.

In a crossover study, 24 healthy individuals who had avoided aspirin for a minimum of 10 days collected random baseline urine specimens. They then took one 81 or 325 mg tablet at 8:00 a.m. and collected a second urine specimen 24 hours after the aspirin was taken. Following a two-week washout period dosages were reversed and another baseline and 24-hours post-aspirin specimen was collected.

Results

Reference Range and Aspirin Values

Individuals taking 81 to 325 mg/day aspirin exhibit a significantly lower mean PURR than those not taking aspirin (Table 2).

TABLE 2

Comparison of mean PURR units for all aspirin users and non-aspirin users.

| | Aspirin therapy | Aspirin non-users | p-value |
|---|---|---|---|
| N | 98 | 159 | |
| Mean | 297 | 1147 | $1.5 \times 10^{-19}$ |
| SD | 330 | 825 | |

EXAMPLE 4

The concept of utilizing 11-dehydrothromboxane measurements to determine individuals in whom aspirin or other platelet modifying compounds is not having a significant platelet inhibiting effect may have several additional applications.

The antigen antibody assay currently performed by conventional ELISA technique could also be performed using a point of care instrument. The test method would have to be modified such that the reaction could take place and the end point be determined within the confines of the point of care instrument.

Additionally, it may be possible to adapt the assay for patient self-testing utilizing "dip stick" technology similar to that used for glucose.

EXAMPLE 5

Urinary Thromboxane $B_2$ Metabolite Monitors the Anti-Platelet Action of Aspirin Concern for side effects and laboratory evidence for aspirin "resistance" in up to 20% of individuals make it essential to establish a simple, effective laboratory monitoring system for aspirin's antithrombotic efficacy. The present example demonstrates the utility of the invention for the purpose in human patients.

11-dehydrothromboxane $B_2$ (11-de-H-$TXB_2$), a stable metabolite of platelet activation was measured in random urine specimens from 65 people who were not taking aspirin and 45 who were taking at least 81 mg/day. The means for non-aspirin users was 2080 pg 11-de-H-TXB$_2$/mg creatinine, and for aspirin users was 523, p.<0.0000.1. Receiver-operating characteristic analysis yields an optimum decision point of 1000 pg 11-de-H-TXB$_2$ in random urine may be used to document aspirin's platelet-suppressive effects and to identify individuals who may not achieve antithrombotic benefits.

EXAMPLE 6

Cadibrants for Use in Assay of Thromboxane B2 Metabolite

It is envisioned that the invention will include a set of calibrating materials that will be used to even better standardize the methods of the invention. These calibrants are described in the present example. In particular, including 1, 2, 3, 4, 5 or more calibrants as described here, in the assay method will improve the consistency of interassay results over time and under a variety of conditions, and will provide reliable, reproduceable, and directly correlateable test results as between different assay patient sample blocks for assessing response to a variety of different doses of aspirin.

In some embodiments, it is envisioned that there will be prepared a set of five different calibrants. These calibrants will provide a reference point metabolite curve. For example, where the set comprises five calibrants, a ready group of five reliable reference points for identifying TxB$_2$ levels in unknown patient urine samples may be assessed. The target values of the calibrant will provide better intra assay standardization, considered to be alike to any biological control material. These "calibrant" control preparations were derived by repeatedly assaying, computing the mean, and the action limits at +/−2 SD. Any single run whose controls i.e., calibrants fall outside the two standard deviation limit is invalidated.

The calibrants of the present invention will also be used to normalize results should systematic error affect assay results. Systematic error may be easily introduced by reagent or instrument changes. Normalizing, i.e. adjusting reported results to a constant, may be accomplished through the application of the calibrants.

Calibrants are urine specimens from individuals with metabolite results that have provided a consistent reading in the present assay, and are spread across the spectrum of possible results. These specimens are aliquotted and frozen at −70 degrees centigrade for long-term storage. Their values are obtained through performance of 25 repeated assays over at least 25 days with subsequent computation of repeat assay means and standard deviations.

In creating the calibrants, urines were selected from people whose previously assayed results were available in the inventor's laboratory. By doing this, samples were selected that had optimum levels representing the whole range. No pooling was performed, rather, individual urines were aliquotted and frozen. Establishing a calibrator in this instance is done by assaying the patent urine sample 20 to 25 times over a minimum of 20 days, then computing the mean and action limits using a 95% confidence interval computation. Eleven to twelve data points for each of the five calibrants have now been created. The means will then serve as target values for subsequent test runs.

| Calibrants 1. TXB2 pg/mL | | | | |
|---|---|---|---|---|
| CJ100 | GE300 | PM500 Dil: 1:2 | EB900 Dil: 1:2 | SS600 Dil: 1:4 |
| 25628 | 55278 | 115812 | 96970 | |
| 26561 | 54710 | 80278 | 100746 | |
| 24332 | 53334 | 104782 | 92484 | |
| 26931 | 54614 | 109228 | 109228 | |
| 27255 | 49114 | 96286 | | |
| | 40651 | 97938 | 87860 | |
| 20623 | 50941 | 109758 | 78924 | 103140 |
| | | | | 108200 |
| | | | | 104244 |
| | | | | 115944 |
| 22864 | 54214 | 118336 | 87618 | |
| | | | | 123520 |
| | | | | 184068 |
| | | | | 102576 |
| 17319 | 35274 | 145844 | 113168 | 116332 |
| | | | | 67924 |
| | | | | 96904 |
| 20790 | 46457 | 99218 | 78852 | 107268 |
| | | | | 99372 |
| Preliminary TXB2 Statistics | | | | |
| N = | 9 | 10 | 10 | 9 | 12 |
| Mean = | 23589.2 | 49458.7 | 107748.0 | 93983.3 | 110791.0 |
| StDev = | 3439.13 | 6796.70 | 17315.51 | 12201.98 | 26862.67 |
| Upper Limit = | 30467.5 | 63052.1 | 142379.0 | 118387.3 | 164516.3 |
| Lower Limit = | 16711.0 | 35865.3 | 73117.0 | 69579.4 | 57065.7 |
| CV % = | 14.6 | 13.7 | 16.1 | 13.0 | 24.2 |

| 2. Creatinine mg/dL | | | | |
|---|---|---|---|---|
| CJ100 | GE300 | PM500 | EB900 | SS600 |
| 116 | 155 | 131 | 97 | |
| 111 | 153 | 139 | 96 | |
| 107 | 157 | 138 | 102 | |
| 114 | 161 | 140 | 96 | |
| 114 | 152 | 133 | 93 | 142 |
| 111 | 149 | 137 | 92 | 135 |
| 119 | 157 | 143 | 100 | 138 |
| 108 | 150 | 134 | 101 | 142 |
| 110 | 118 | 133 | 90 | 134 |
| 101 | 147 | 129 | 87 | 128 |
| 111 | 147 | 137 | 101 | 144 |
| Creatinine Statistics | | | | |
| N = | 11 | 11 | 11 | 11 | 7 |
| Mean = | 111.1 | 149.6 | 135.8 | 95.9 | 137.6 |
| StDev = | 4.83 | 11.40 | 4.19 | 4.95 | 5.65 |
| Upper Limit = | 120.7 | 172.4 | 144.2 | 105.8 | 148.9 |
| Lower Limit = | 101.4 | 126.8 | 127.4 | 86.0 | 126.3 |
| CV % = | 4.3 | 7.6 | 3.1 | 5.2 | 4.1 |

| 3. PURR | | | | |
|---|---|---|---|---|
| CJ100 | GE300 | PM500 | EB900 | SS600 |
| 231 | 369 | 853 | 1011 | |
| 239 | 366 | 591 | 1050 | |
| 219 | 356 | 771 | 964 | |
| 242 | 365 | 804 | 1139 | |

-continued

| | | | | |
|---|---|---|---|---|
| 245 | 328 | 709 | | |
| | 272 | 721 | 916 | |
| 186 | 340 | 808 | 823 | 750 |
| | | | | 787 |
| | | | | 758 |
| | | | | 843 |
| 206 | 362 | 871 | 914 | |
| | | | | 898 |
| | | | | 1338 |
| | | | | 746 |
| 156 | 236 | 1074 | 1180 | 846 |
| | | | | 494 |
| | | | | 704 |
| 187 | 310 | 731 | 822 | 780 |
| | | | | 722 |

| Preliminary PURR Statistics | | | | | |
|---|---|---|---|---|---|
| N = | 9 | 10 | 10 | 9 | 12 |
| Mean = | 212.3 | 330.5 | 793.3 | 979.9 | 805.3 |
| StDev = | 30.96 | 45.42 | 127.49 | 127.22 | 195.26 |
| Upper Limit = | 274.3 | 421.4 | 1048.3 | 1234.4 | 1195.9 |
| Lower Limit = | 150.4 | 239.7 | 538.3 | 725.5 | 414.8 |
| CV % = | 14.6 | 13.7 | 16.1 | 13.0 | 24.2 |

The following designation of calibrants as envisioned by the inventors represents at least one of the embodiments of the invention.

Calibrant 1—(Low)
Calibrant 2—(Medium-Low)
Calibrant 3—(Medium)
Calibrant 4—(Medium High)
Calibrant 5—(High)

It is anticipated that calibrants for use in the assessment of aspirin response as part of the present assay will be created from other than human urine, and thus are not limited to human urine calibrants alone.

EXAMPLE 7

Combination Therapies of Aspirin Together with Neutraceuticals

Aspirin, through its antiplatelet effect, reduces the risk of cardiovascular disease in most high-risk individuals. However, evidence of aspirin resistance in up to 20% of individuals makes it essential to establish a simple, effective laboratory monitoring system for aspirin's antiplatelet activity. The ability to monitor aspirin's antiplatelet effect may be mitigated by the effects of dietary components, and in particular by that group of compounds known as neutraceuticals. By way of example, that group of compositions known to comprise neutraceuticals includes purple grape juice, supplements such as vitamin E, St. Johns Wort, and the like.

11-dehydro thromboxane $B_2$, a stable metabolite of platelet-specific cyclooxygenase activity, in urine specimens from 29 individuals was measured. Participants were instructed to drink controlled daily volumes of purple grape juice, 400 international units per day of vitamin E, and 650 mg per day of aspirin. Each intervention was given in one-week intervals separated by a one-week washout period. The metabolite was measured in baseline, post-intervention, and post-washout urine specimens and the results were expressed as platelet urinary response ratios (PURR) based upon pg 11-dehydrothromboxane $B_2$/mg creatinine. Results are shown in the table. Vitamin E has no measurable effect, grape juice has a small but significant effect, and aspirin has a large and statistically significant effect upon urinary excretion of the platelet cyclooxygenase metabolite 11-dehydro thromboxane $B_2$.

Other non-steroidal anti-inflammatory drugs (NSAIDs) such as acetaminophen, dipyriadamole, sulphinpyrazone, or ibuprofen act upon COX-1 or other platelet enzymes. Ticlopidine, clopidegril, and abciximab exert their antigometry on plasma, serum, and in urine $TXB_2$ assays.

Many dietary components and supplements have been shown to modify platelet function by unknown mechanisms. These include fish oil, vitamin E, garlic, red wine, and purple grape juice. Herbal and dietary supplements may both interfere with or enhance the effect of aspirin on platelets. Therefore, when used in combination with the present invention, the particular patient's aspirin dose response and clinical condition would be considered in deciding to place the patient on a regimen that includes certain neutraceuticals, or that excludes others.

TABLE 3

| Weber Donor | Baseline | Post-Grape Juice | First Washout | Second Washout | Mean Baseline |
|---|---|---|---|---|---|
| 001 | 1349 | 1469 | 774 | 1355 | 1159 |
| 002 | 1058 | 857 | 936 | 1211 | 1069 |
| 003 | 911 | 1070 | 1588 | | 1250 |
| 004 | 917 | 649 | 913 | 758 | 863 |
| 005 | 708 | | 811 | 754 | 758 |
| 006 | 1269 | 664 | 1600 | 1106 | 1325 |
| 007 | 867 | 585 | 461 | 669 | 666 |
| 009 | 723 | 796 | 977 | 915 | 872 |
| 010 | 865 | 830 | 1083 | 902 | 950 |
| 011 | 1578 | 901 | 1748 | 1449 | 1591 |
| 012 | 1725 | 1505 | 1631 | 2009 | 1788 |
| 014 | 786 | 1437 | 627 | | 707 |
| 015 | 1151 | 816 | 956 | 1046 | 1051 |
| 016 | | 689 | 801 | | 801 |
| 017 | 989 | 384 | 435 | 756 | 727 |
| 018 | 608 | 796 | 843 | 743 | 731 |
| 019 | 744 | 1387 | 1490 | 829 | 1021 |
| 021 | 828 | 466 | 887 | 843 | 852 |
| 022 | 965 | 746 | 1598 | | 1282 |
| 023 | 1809 | 654 | 871 | | 1340 |
| 024 | 1034 | 463 | 449 | 506 | 663 |
| 025 | 670 | 833 | 541 | 1228 | 813 |
| 026 | 2168 | 1763 | 1847 | | 2007 |
| 027 | 1730 | 937 | 945 | 1345 | 1340 |
| 029 | 639 | 948 | 611 | 825 | 692 |
| 030 | 3604 | 1391 | 1792 | | 2698 |
| 031 | 874 | 750 | | | 874 |
| 033 | 850 | 911 | 1312 | | 1081 |
| 034 | 1071 | 1290 | | | 1071 |
| N | 28 | 28 | 27 | 19 | 29 |
| Mean | 1160.3 | 920.9 | 1056.6 | 1013.1 | 1105 |
| SD | 623.1 | 359.3 | 448.8 | 355.1 | 456.5 |

Percent reduction: 16.6

The reduction of 16.6% post grape-juice is significant at $p < 0.05$ for the one-tail test.

t-Test: Two-Sample Assuming Equal Variances

Mean Baseline to Post-Grape Juice

| | Variable 1 | Variable 2 |
|---|---|---|
| Mean | 1104.827671 | 920.9479068 |
| Variance | 208394.0792 | 129070.2794 |
| Observations | 29 | 28 |
| Pooled Variance | 169453.3048 | |
| Hypothesized Mean Difference | 0 | |
| df | 55 | |

-continued

|  | Variable 1 | Variable 2 |
|---|---|---|
| r Stat | 1.685968679 | |
| P(T <= t) one-tail significant at <0.05 | 0.048733764 | |
| t Critical one-tail | 1.673033694 | |
| P(T <= t) two-tail | 0.097467528 | |
| I Critical two-tail | 2.004044291 | |

TABLE 4

|  | Mean Baseline | Mean Post-Grape Juice | Mean Post-Vitamin E | Mean Post-Aspirin |
|---|---|---|---|---|
| N: | 29 | 28 | 26 | 19 |
| PURR: | 1105 | 920.9 | 1293.1 | 379.7 |
| % Change: |  | −16.6% | +14.3% | −65.6% |
| P: |  | 0.049* | 0.113 | $2.365 \times 10^{-7}$* |

Significant at P < 0.05
Additional platelet activity-suppressing substances

EXAMPLE 8

Baseline for Positive Aspirin Response

The present example describes another embodiment of the method by which the response to aspirin may be assessed. It was discovered that by changing the buffer that was used to prepare the test urine sample, the cut-off for identifying a response to the aspirin could be further defined, and reduced to a value of about 400 pg.

The PURRs generated in the 11-dehydro thromboxane $B_2$ assay in the present example were higher than those generated in subsequent studies. The average reduction after the investigators initial assay was 60%. This change was a result of a reformulation of the reagent buffer. Reformation of the buffer was made by the supplier, Cayman Chemical Corporation. The initial buffer was thought to be a phosphate saline buffer. The reformatted buffer is an alpha diethanolamine buffer. Cayman Chemical indicates that the antibody used in the test is only reactive with the free acid form of the 11-dehydro thromboxane $B_2$. The buffer change was made to convert any lactone form present in the same urine to the free acid form of the thromboxane. The current procedure requires a two-hour pre-incubation of the urine sample in the diethanolamine buffer in order to allow for the conversion of the forms before pipetting to the plate. The new decision point for the assay is 400 PURR units, down from the original 1000.

Neutraceuticals may mimic aspirin's activity and therefore cause aspirin-like results in the assay. Thus, ASPIR-INcheck patients may be cautioned to discontinue these for a few days. Neither Vitamin E nor grape juice has had such an effect. More dietary supplements, including garlic, ginko biloba, and St. John's Wort will be made. Perhaps a supplement that closely mimics the anti-platelet effect of aspirin will be identified. If so, it may be used as an adjunct or alternative to aspirin therapy, and would be considered an additional embodiment of the invention, such as in a combination therapy, and would be considered an additional embodiment of the invention, such as in a combination therapy method.

EXAMPLE 9

Platelet Urinary Response Ratio (PURR)

To normalize for urinary output, results are expressed as platelet urinary response ratio (PURR) based upon pg 11-dehydro $TXB_2$/g creatinine. Results of all populations were compared using the student t-test.

Effect of Aspirin on 11-dehydro $TXB_2$ in Healthy Non-Aspirin Users

In a crossover study, twenty-four healthy individuals who had avoided aspirin for a minimum of ten days collected random baseline urine specimens. They then took one 81 or 325 mg tablet at 8:00 AM and collected a second urine specimen 24 hours after the aspirin was taken. Following a 2-week washout period dosages were reversed and another baseline and 24-hours post-aspirin specimen was collected.

Effect of Aspirin on the PURR of Healthy Non-Aspirin Users

Figure 7:
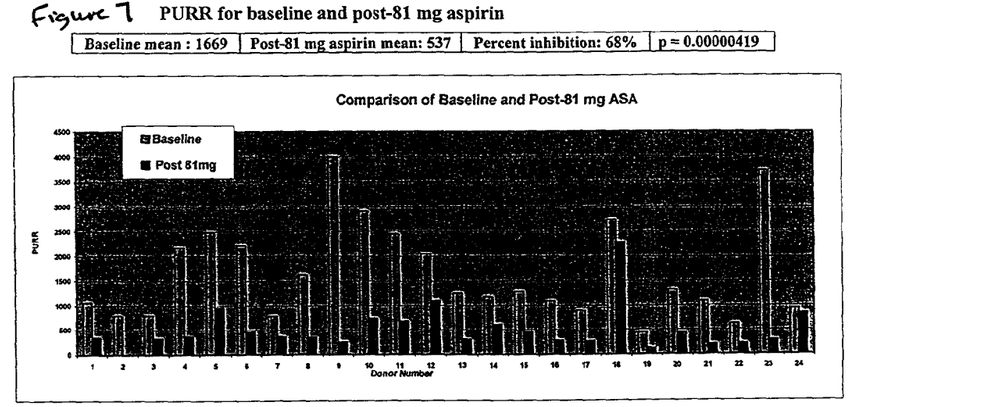
Figure 8:
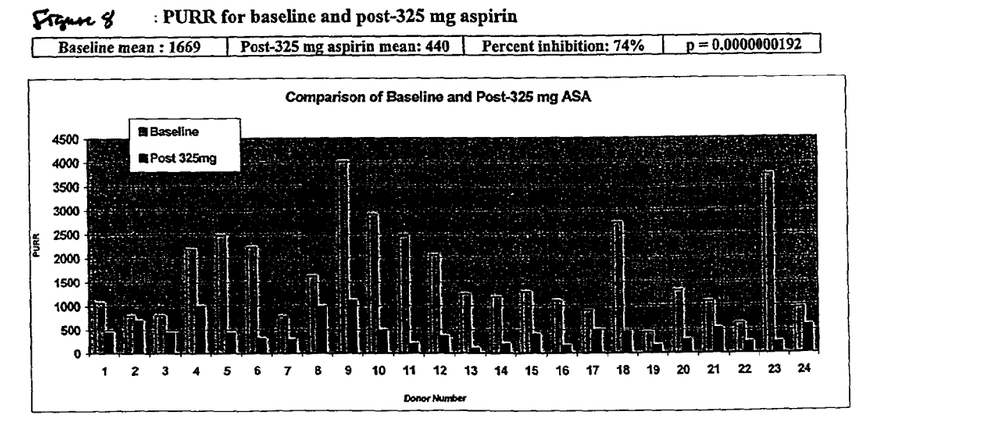
Figure 9:
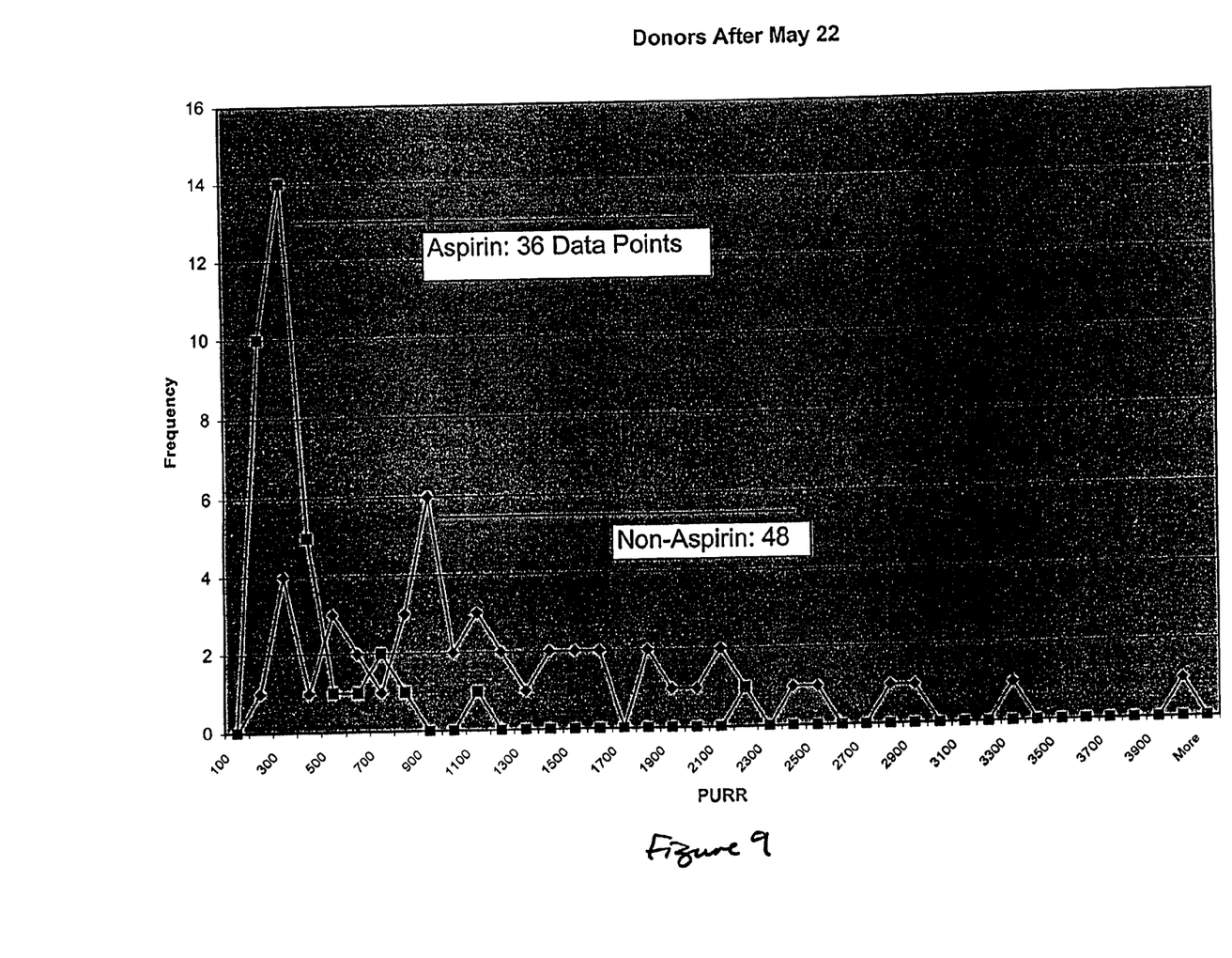
Figure 10:
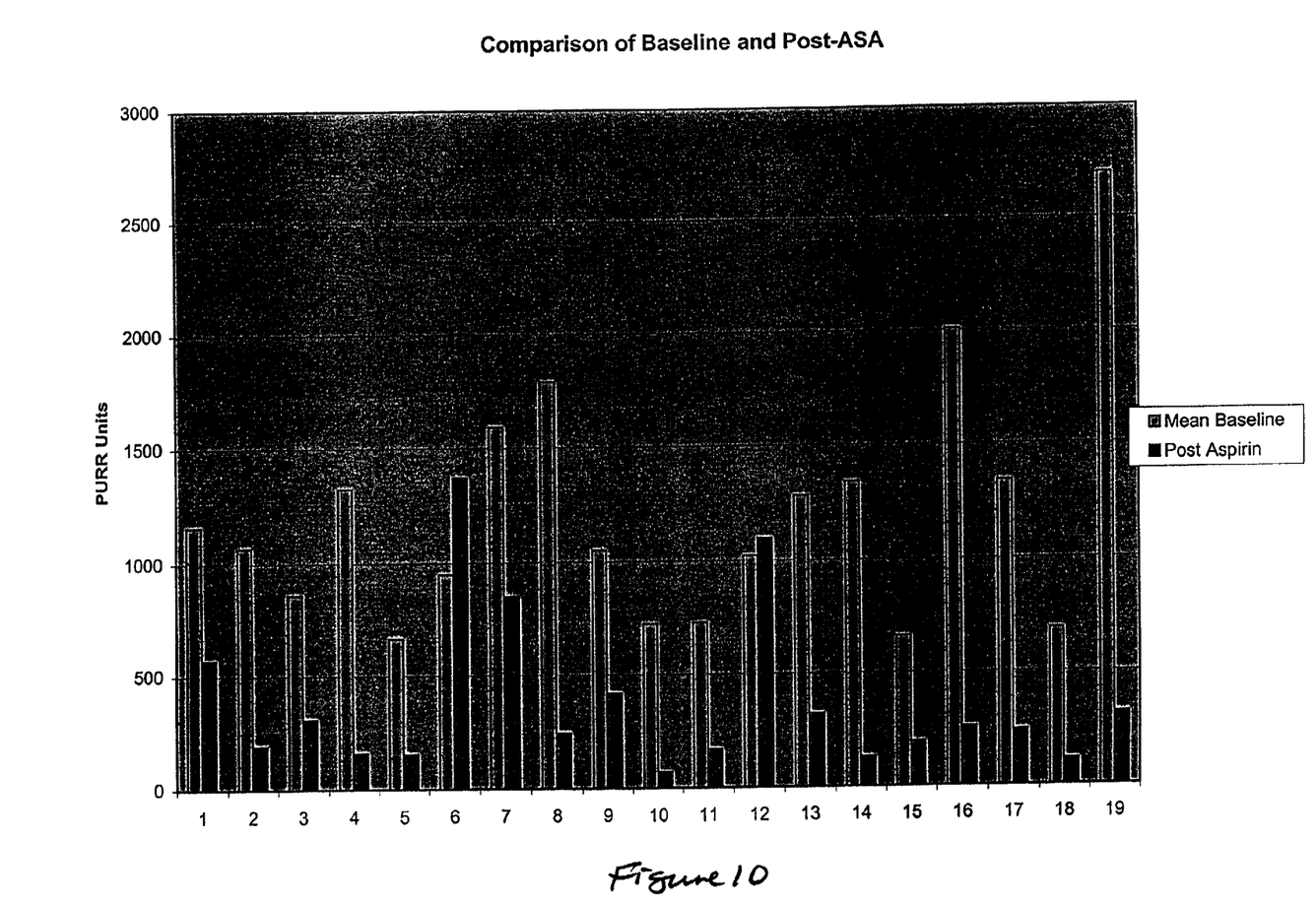
FIG. 10—Subjects with a <50% response to aspirin in pg/mg and percent inhibition—Histogram Comparison of Aspirin and Non-Aspirin Donors.

Initiation of aspirin therapy causes mean reduction of 68% for 81 mg/day and 76% for 325 mg/day as illustrated in FIGS. 7 and 8. There was no significant difference between the 81 mg/day and 325 mg/day suppression levels. Data was generated using a different formulation, this accounts for the higher range of PURR units.

Results

Reference Range and Aspirin Values

Individuals taking 81 to 325 mg/day aspirin exhibit significantly lower levels of 11-dehydro-$TXB_2$ than those not taking aspirin See Table 5.

TABLE 5

| Comparison of mean PURR units for all aspirin users and non-aspirin users. | | | |
|---|---|---|---|
|  | Aspirin therapy | Aspirin non-users | p-value |
| N | 98 | 159 |  |
| Mean | 297 | 1147 | $1.5 \times 10^{19}$ |
| SO | 330 | 825 |  |

TABLE 6

| | | | | | | | | | | | | |
|---|---|---|---|---|---|---|---|---|---|---|---|---|
| Determining the decision point by computing and comparing error rates establishes the recommended decision point of 400 PURR Units | | | | | | | | | | | | |
| All data | Decision level in Platelet Urinary Response Ratio | False positives; non-ASAs in ASA range | True positives; ASAs in ASA range | False negatives; ASAs in non-ASA range | True negatives; non-ASAs in non-ASA range | Total ASAs | Total non-ASAs | False positive % for aspirin effect | True positive % (sensitivity) for aspirin effect | False negative % for aspirin effect | True negative % (specificity) for aspirin effect | Total FP % and FN % |
|  | 200 | 3 | 50 | 48 | 156 | 98 | 159 | 1.9 | 51.0 | 49.0 | 98.1 | 50.9 |
|  | 250 | 5 | 61 | 37 | 154 | 98 | 159 | 3.1 | 62.2 | 37.8 | 96.6 | 40.9 |

TABLE 6-continued

Determining the decision point by computing and comparing error rates establishes the recommended decision point of 400 PURR Units

| All data | Decision level in Platelet Urinary Response Ratio | False positives; non-ASAs in ASA range | True positives; ASAs in ASA range | False negatives; ASAs in non-ASA range | True negatives; non-ASAs in non-ASA range | Total ASAs | Total non-ASAs | False positive % for aspirin effect | True positive % (sensitivity) for aspirin effect | False negative % for aspirin effect | True negative % (specificity) for aspirin effect | Total FP % and FN % |
|---|---|---|---|---|---|---|---|---|---|---|---|---|
|  | 300 | 9 | 70 | 28 | 150 | 98 | 159 | 5.7 | 71.4 | 28.6 | 94.3 | 34.2 |
|  | 350 | 11 | 77 | 21 | 148 | 98 | 159 | 6.9 | 78.6 | 21.4 | 93.1 | 28.3 |
| Decision Point | 400 | 16 | 81 | 17 | 143 | 98 | 159 | 10.1 | 82.7 | 17.3 | 89.9 | 27.4 |
| Repeat Analysis | 450 | 22 | 83 | 15 | 137 | 98 | 159 | 13.8 | 84.7 | 15.3 | 86.2 | 29.1 |
| Repeat Analysis | 500 | 23 | 85 | 13 | 135 | 98 | 159 | 14.5 | 86.7 | 13.3 | 85.5 | 27.7 |
|  | 550 | 30 | 86 | 12 | 129 | 98 | 159 | 18.9 | 87.8 | 12.2 | 81.1 | 31.1 |
|  | 600 | 36 | 88 | 10 | 123 | 98 | 159 | 22.6 | 89.8 | 10.2 | 77.4 | 32.8 |

Results

Individuals taking 81 mg/day to 325 mg/day aspirin exhibit a significantly lower mean PURR than those not taking aspirin.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents, which are both chemically and physiologically, related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Juul-Moler S., Edvardsson N., Jahnmatz B., et al., *Lancet* 1992; 340: 1421.
2. The RISC Group, *Lancet* 1992; 340: 1421.
3. ISIS-2 Collaborative Group; ISIS-2, *Lancet* 1988; 2: 349
4. The Dutch TIA Study Group, *N. Engl. J. Med.* 1991; 325: 1261.
5. Hirsh J., Dalen J. E., Fuster V., Harker L. B., Patrono C., Roth G., *Chest* 1995; 108 Suppl.: 247s.
6. International Stroke Trial Collaborative Group, *Lancet* 1997; 349: 1569.
7. CAST (Chinese Acute Stroke Trial) Collaborative Group, *Lancet* 1997; 349: 1641.
8. The Medical Research Council's General Practice Research Framework, *Lancet* 1998; 351: 233.
9. Hansson L., Zanchatti A., Carruthers S. G., et al., *Lancet* 1998; 351: 1755.
10. Fitch L. L., Buchwald H., Matts J. P., *Am. Heart J.* 1995; 129: 656.
11. Antiplatelet Trialists' Collaboration, *BMJ* 1994; 308: 81.
12. Hennekens C. H., Peto R., Hutchinson G. B., et al., *N. Engl. J Med.* 1988; 318: 923.
13. Manson J. E., Stampfer M. J., Colditz G. A., et al., *JAMA* 1991; 266: 521.
14. Ridker P. M., Manson J. E., Buring J. E., Muller J. E., Hennekens C. H., *Circulation* 1990; 82: 897.
15. Buring J. E., Hennekens C. H., *J Myocardial Ischemia* 1992; 4: 27.
16. Roderick P. J., Wilkes H. C., Meade T. W., *Br. J. Clin. Pharmacol* 1993; 35: 219.
17. Petroski D., *Lancet* 1997; 349: 430.
18. Petro R., Gray R., Collins R., et al., *BMJ* 1988; 296: 313.
19. Kronmal R. A., Hart R. G., Manolio T. A., *Stroke* 1998; 29: 887.
20. He J., Whelton P. K., Vu B., Klag M. J., *JAMA* 1998; 280: 1930.
21. Patrono C., Coller B., Dalen J., et al., *Chest* 1998; 114 Suppl.: 470s.
22. Helgason C. M., Hoff J. A., Kondos G. T., Brace L. D., *Stroke* 1993; 24: 1458.
23. Ridker P. M., Cushman M., Stampfer M. J., Tracy R. P., Hennekens C. H.
24. Wu K. K., Hoak J. C., *Lancet II;* 1974: 924.
25. Trip M. D., Cats V. M., Van Capelle F. J. L., Vreeken J., *New Engl. J. Med.* 1990, 322: 1549.
26. Helgason C. M., Bolin K. M., Hoff J. A., et al., *Stroke* 1994; 25: 2331.
27. Pappas J. M., Westengard J. C., Bull B. S., *Arch. Path. Lab. Med.* 1994; 118: 801.
28. Mueller M. R., Salat A., Stangl P., *Thromb. Haemost* 1997; 78: 1003.
29. Grotemeyer K. H., Scharafinski H. W., Husstedt I. W., *Thrombos. Res.* 1993; 71: 397.
30. Komiya T., Kudo M., Urabe T., Mizuno Y., *Stroke* 1994; 25: 2337.
31. Israels L. G.
32. Rifkin R. M.,
33. Vane J. R., Botting R. M., *Semin. Arthr. Rheum.* 1997; 25 Suppl. I: 2.
34. Lawson J. A., Patrono C., Ciabattone G., et al., *Anal. Biocem.* 1986, 155: 198.

35. Schror K., *Semin. Thrombos. Hemostas.* 1997; 23: 349.
36. Weber A. A., Zimmermann K. C., Meyer-Kirchrath J., Schror K., *Lancet* 1999; 353: 900.
37. Pedersen A. K., Fitzgerald G. A., *New Engl. J. Med.* 1984; 311: 1206.
38. Schmidt E. B., Dyerberg J., *Drugs* 1994; 47: 405.
39. Weber P., Dendich A., Machlin L. J., *Nutr.* 1997; 13: 450.
40. O'neil C. K., Avila J. R., Fetrow C. W., *Nursing* 1999; 58.
41. Rotondo S., Rotilio D., Cerletti C., De Gaetano G., *Thrombos Haemostas* 1994; 72: 813.
42. Jannsen P. L. T. M. K., Akkerman J.-W. N., Hollman P. C. H., Van Staveren W. A., Zwaginga J-J, Katan M. B., *Eur. J. Clin. Nutr.* 1995; 49: 365.
43. Beving H., Eksborg S., Malingren R. S., et al., *Thrombos. Res.* 1994; 74: 39.
44. Buerke M., Pittroff W., Meyer J., Darius H., *Am. Heart J* 1995; 130: 465.
45. May J. A., Heptinstall S., Cole A. T., Hawkey C. J., *Thrombos. Res.* 1997; 88: 183.
46. Samuelsson B., Granstrom E., Green K., et al., *Ann. Rev. Biochem.* 1975; 44: 669.
47. Catella F., Fitzgerald G. A., *Thrombos. Res.* 1987; 47: 647.
48. Catella F., Healy D., Lawson J. A., et al., *Proc. Natl. Acad. Sci. USA* 1986; 83: 5861.
49. Van Kooten F., Ciabattoni G., Koudstaal P. J., Dippel W. J., Patrono C., *Stroke* 1999; 30:546.
50. Lellouche F., Fradin A., Fitzgerald G., et al., *Prostaglandins* 1990; 40: 297.

What is claimed is:

1. A kit for monitoring blood platelet activation comprising:
   a) a substrate having attached thereto an antibody which binds to a thromboxane B2 metabolite to form an antibody-metabolite complex;
   b) a first color-indicator capable of reacting with said antibody-metabolite complex; and
   c) a second color indicator which reacts with creatinine.

2. The kit of claim 1, further comprising an instruction sheet.

3. The kit of claim 2, wherein the thromboxane $B_2$ metabolite is 11-dehydrothromboxane $B_2$.

4. The kit of claim 2, further comprising at least one calibrant comprising urine with a known level of thromboxane $B_2$ metabolite.

5. The kit of claim 4, wherein the urine is human urine.

6. The kit of claim 4, wherein the thromboxane $B_2$ metabolite is 11-dehydrothromboxane $B_2$.

7. An assay kit for assessing dose response to aspirin comprising:
   a) at least one calibrant comprising urine with a known amount of thromboxane B2 metabolite;
   b) an antibody which binds to the thromboxane $B_2$ metabolite to form an antibody-metabolite complex;
   c) a first color-indicator which reacts with said antibody-metabolite complex; and
   d) a second color indicator which reacts with creatinine.

8. The assay kit of claim 7, wherein the thromboxane $B_2$ metabolite is 11-dehydrothromboxane $B_2$.

9. The assay kit of claim 7, wherein the calibrant comprises a set of human urine calibrants, each having a different level of thromboxane B2 metabolite.

10. The assay kit of claim 9, wherein the set of calibrants comprises at least three calibrants.

11. The assay kit of claim 10, further comprising instructions for use of the assay kit.

12. The assay kit of claim 11, wherein said antibody is attached to a solid substrate.

* * * * *